(12) United States Patent
Kang et al.

(10) Patent No.: US 8,569,200 B2
(45) Date of Patent: Oct. 29, 2013

(54) CATALYST FOR HYDROCARBON STEAM CRACKING, METHOD OF PREPARING THE SAME AND METHOD OF PREPARING OLEFIN BY USING THE SAME

(75) Inventors: Jun-han Kang, Daejeon (KR); Jong-hun Song, Daejeon (KR); Jun-seon Choi, Daejeon (KR); Byoung-gi Park, Jeollanam-do (KR); Chang-hoon Kang, Yeosu-Si (KR); Si-hyun Noh, Yeosu-Si (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 13/309,241

(22) Filed: Dec. 1, 2011

(65) Prior Publication Data

US 2012/0108416 A1 May 3, 2012

Related U.S. Application Data

(62) Division of application No. 12/154,656, filed on May 23, 2008, now Pat. No. 8,123,931.

(30) Foreign Application Priority Data

May 25, 2007 (KR) .................. 10-2007-0050975

(51) Int. Cl.
*B01J 21/06* (2006.01)
(52) U.S. Cl.
USPC ........... 502/309; 502/305; 502/308; 502/312; 502/314; 585/648; 585/650; 585/651; 585/652; 585/653
(58) Field of Classification Search
USPC .......... 502/308, 309, 312, 314, 315; 585/648, 585/650, 651, 652, 653; 208/106, 113, 121, 208/122, 123, 132
See application file for complete search history.

(56) References Cited

U.S. PATENT DOCUMENTS 3,488,402 A * 1/1970 Baudino et al. ............... 585/617
3,520,656 A * 7/1970 Yates et al. .................... 423/345

(Continued)

FOREIGN PATENT DOCUMENTS

EP   0 212 320      3/1987
KR   20020048774 A  6/2002

(Continued)

OTHER PUBLICATIONS

U.S. Appl. No. 12/154,656.

(Continued)

*Primary Examiner* — In Suk Bullock
*Assistant Examiner* — Bradley Etherton
(74) *Attorney, Agent, or Firm* — Lerner, David, Littenberg, Krumholz & Mentlik, LLP (57) ABSTRACT

A catalyst for hydrocarbon steam cracking for the production of light olefin, a preparation method of the catalyst and a preparation method of olefin by using the same. More precisely, the present invention relates to a composite catalyst prepared by mixing the oxide catalyst powder represented by CrZrjAkOx ($0.5 \leq j \leq 120$, $0 \leq k \leq 50$, A is a transition metal, x is the number satisfying the condition according to valences of Cr, Zr and A, and values of j and k) and carrier powder and sintering thereof, a composite catalyst wherein the oxide catalyst is impregnated on a carrier, and a method of preparing light olefin such as ethylene and propylene by hydrocarbon steam cracking in the presence of the composite catalyst. The composite catalyst of the present invention has excellent thermal/mechanical stability in the cracking process, and has less inactivation rate by coke and significantly increases light olefin yield.

11 Claims, 2 Drawing Sheets

(56) References Cited

U.S. PATENT DOCUMENTS

| | | | |
|---|---|---|---|
| 3,644,557 A | | 2/1972 | Senes et al. |
| 3,725,495 A | * | 4/1973 | Wrisberg et al. ............. 585/414 |
| 3,839,485 A | | 10/1974 | Wrisberg et al. |
| 3,846,340 A | * | 11/1974 | Okuyama et al. ............... 502/84 |
| 3,872,179 A | | 3/1975 | Andersen et al. |
| 3,945,946 A | * | 3/1976 | Hindin et al. ................. 502/308 |
| 3,969,542 A | | 7/1976 | Tomita et al. |
| 4,003,978 A | * | 1/1977 | Shiraishi et al. ............. 423/237 |
| 4,111,793 A | | 9/1978 | Kolombos et al. |
| 4,269,737 A | * | 5/1981 | Grenoble et al. ............. 502/204 |
| 4,692,306 A | | 9/1987 | Minet et al. |
| 4,769,224 A | * | 9/1988 | van Grinsven et al. ....... 423/236 |
| 5,053,577 A | | 10/1991 | Teller et al. |
| 5,378,350 A | | 1/1995 | Zimmermann et al. |
| 5,600,051 A | | 2/1997 | Baker et al. |
| 5,660,807 A | * | 8/1997 | Forg et al. ..................... 423/236 |
| 6,224,748 B1 | | 5/2001 | Chang et al. |
| 7,022,643 B2 | | 4/2006 | Yunoki et al. |
| 7,026,263 B2 | | 4/2006 | Le Van Mao et al. |
| 7,232,780 B2 | | 6/2007 | Zhu et al. |
| 7,288,691 B2 | | 10/2007 | Martin et al. |
| 2003/0180473 A1 | | 9/2003 | Nishihara et al. |
| 2005/0234283 A1 | | 10/2005 | Xu et al. |
| 2005/0245387 A1 | | 11/2005 | Zhu et al. |
| 2008/0081008 A1 | | 4/2008 | Choi et al. |

FOREIGN PATENT DOCUMENTS

| | | |
|---|---|---|
| KR | 20030083924 A | 11/2003 |
| KR | 20040016552 A | 2/2004 |
| KR | 20040101868 A | 12/2004 |
| KR | 20050016708 | 2/2005 |
| KR | 2006-0055366 A | 5/2006 |
| RU | 1011236 | 1/2000 |
| WO | 2004105939 A1 | 12/2004 |

OTHER PUBLICATIONS

U. S. Appl. No. 12/217,246.
Takita et al. "Catalytic decomposition of CFCs", Catalysis Surveys from Japan 2 (1998) 165-173.
Sohn et al. "Surface Characterization of Chromium Oxide-Zirconia Catalyst" Langmuir 1993 9, 126-131.
Office Action and Response from U.S. Appl. No. 11/902,665 dated May 11, 2010.
U.S. Appl. No. 11/902,665.
Gates, "Catalysis" in Kirk-Othmer Encyclopedia of Chemical Technology, John Wiley, 2002, published on-line Aug. 16, 2002.
Lemonidou, et al., "Catalyst Evaluation and Kinetic Study for Ethylene Production" in Ind. Eng. Chem. Res., 1989, 28, 524-530.
Towfighi, et al., "Steam Cracking of Naphtha in Packed Bed Reactors" in Ind. Eng. Chem. Res., 2002, 41, 1419-1424.

* cited by examiner

CATALYST FOR HYDROCARBON STEAM CRACKING, METHOD OF PREPARING THE SAME AND METHOD OF PREPARING OLEFIN BY USING THE SAME

CROSS REFERENCE TO RELATED APPLICATIONS

The present application is a divisional of U.S. patent application Ser. No. 12/154,656, filed May 23, 2008, the disclosure of which is incorporated herein in its entirety by reference. The present application claims the benefit of the filing date of Korean Patent Application No. 10-2007-0050975 filed on May 25, 2007 in the Korean Intellectual Property Office, the disclosure of which is incorporated herein in its entirety by reference.

TECHNICAL FIELD

The present invention relates to a catalyst for hydrocarbon steam cracking for the production of light olefin, a preparation method of the catalyst and a preparation method of olefin by using the same. More precisely, the present invention relates to a catalyst for hydrocarbon steam cracking which gives improved yield of light olefin and has thermal/mechanical stability at high temperature for the production of light olefin by hydrocarbon steam cracking, a preparation method of the catalyst and a preparation method of light olefin using the catalyst.

BACKGROUND ART

Important raw materials necessary for the production of petroleum products such as ethylene and propylene are prepared by hydrocarbon steam cracking which is a major ingredient of natural gas or paraffin compounds such as naphtha and gas oil, at high temperature of at least 800° C. in the presence of water vapor.

To increase the yield of ethylene or propylene from hydrocarbon steam cracking, it has been largely attempted to increase hydrocarbon conversion rate or to increase olefin selectivity. However, there is a limitation in increasing hydrocarbon conversion rate or olefin selectivity depending only on steam cracking. So, alternatives have been proposed to increase olefin yield.

For example, using a catalyst for steam cracking was proposed as an alternative for the improvement of ethylene and propylene yields from hydrocarbon steam cracking. U.S. Pat. No. 3,644,557 describes the catalyst composed of magnesium oxide and zirconium oxide, U.S. Pat. No. 3,969,542 describes the catalyst containing calcium aluminate as a basic component, U.S. Pat. No. 4,111,793 describes the manganese oxide catalyst impregnated in zirconium oxide, European Patent Publication No. 0212320 describes the iron catalyst impregnated in magnesium oxide, and U.S. Pat. No. 5,600,051 describes the catalyst composed of barium oxide, alumina and silica. PCT No. 2004/105939 describes a method using the catalyst composed of potassium magnesium phosphate, silica and alumina. It has been known that these catalysts are acting as a heating medium during hydrocarbon steam cracking to increase olefin yield, but the increase of olefin yield is not satisfactory compared with when an inactive carrier is used.

Russian Patent No. 1,011,236 describes the potassium vanadate catalyst modified with boron oxide carried in an alumina carrier. However, using the potassium vanadate catalyst or alkali metal oxide experiences not only unsatisfactory improvement of olefin yield but also loss at high temperature for hydrocarbon decomposition. That is, the components of the catalysts have low melting points and thus exist possibly in liquid phase in the inside of a high-temperature cracking reactor and they are easily evaporated owing to the fast gas flow during the reaction, resulting in the loss of catalytic activity as reaction progresses.

U.S. Pat. No. 7,026,263 describes a method of using a hybrid catalyst composed of molybdenum oxide, alumina, silica, silicalite and zirconium oxide. The catalyst has an advantage of usability at low temperature reaction, but at the same time has a disadvantage of difficulty in direct addition to the actual production line because it is used at a very low hydrocarbon superficial velocity. In addition, thermostability of such catalyst becomes very low at the reaction temperature of 700~800° C. or up, resulting in the loss of catalytic activity.

Most of the conventional cracking processes are performed at a high reaction temperature and with a high hydrocarbon superficial velocity and accompany the generation of a huge amount of coke. The generated coke has to be burned at a high temperature. To utilize a catalyst for a long time under such a severe condition, the catalyst has to be thermally/physically stable with less transformation. However, the above methods and skills are in question of thermal/physical stability.

To prevent economical loss in the process of hydrocarbon steam cracking and to avoid complicated production processes, an excellent catalyst which is capable of improving the yield of light olefin higher than an inactive carrier can do and is thermally/mechanically stable at high temperature is required.

DISCLOSURE OF THE INVENTION

It is an object of the present invention, to overcome the above problems of the conventional art, to provide a catalyst for hydrocarbon steam cracking which has excellent thermostability at high temperature and improves olefin yield and selectivity from hydrocarbon steam cracking and at the same time has low inactivation rate by coke, more precisely a composite catalyst prepared by sintering the mixture of the oxide catalyst powder represented by $CrZr_jA_kO_x$ and carrier powder, and a composite catalyst having the structure where the oxide catalyst is impregnated on a carrier.

It is another object of the present invention to provide a method for preparing a composite catalyst prepared by sintering the mixture of the oxide catalyst powder represented by $CrZr_jA_kO_x$ and carrier powder, and a composite catalyst having the oxide catalyst impregnated on a carrier.

It is also an object of the present invention to provide a method for preparing olefin by hydrocarbon steam cracking in the presence of the catalyst.

The above objects and other objects of the present invention can be achieved by the following embodiments of the present invention.

The present invention is described in detail hereinafter.

To achieve the above objects, the present invention provides a catalyst for hydrocarbon steam cracking, which contains a composite catalyst prepared by sintering the mixture of the oxide catalyst represented by $CrZr_jA_kO_x$ ($0.5 \leq j \leq 120$, $0 \leq k \leq 50$, A is a transition metal, x is the number satisfying the condition according to valences of Cr, Zr and A, and values of j and k) and carrier powder.

The present invention also provides a catalyst for hydrocarbon steam cracking which contains a composite catalyst having the oxide catalyst represented by $CrZr_jA_kO_x$ ($0.5 \leq j \leq 120$, $0 \leq k \leq 50$, A is a transition metal, x is the number satisfying the condition according to valences of Cr, Zr and A, and values of j and k) impregnated on a carrier.

At this time, A of the oxide is one or more selected from the group consisting of Ti, Nb, Mo, V, Co, Ni, W, Fe and rare earth metals, and Ti is preferred.

The carrier is selected from the group consisting of alpha alumina, silica, silica-alumina, zirconium oxide, magnesium oxide, magnesium aluminate, calcium aluminate, silicon carbide, aluminum titanate and zeolite, and silicon carbide is preferred.

The present invention provides a method for preparing a catalyst for hydrocarbon steam cracking comprising the following steps: (a) preparing an aqueous solution by mixing Cr containing compound and Zr containing compound or Cr—Zr containing compound with water; (b) preparing a slurry by co-precipitation after adding ammonia water to the prepared aqueous solution; (c) heat-refluxing or hydrothermal-treating the slurry; (d) preparing an oxide catalyst by filtering, drying and calcining the slurry; (e) preparing a composite catalyst by sintering the mixture of the oxide catalyst powder and carrier powder; (f) molding the composite catalyst; and (g) sintering the molded composite catalyst.

The present invention also provides a method for preparing a catalyst for hydrocarbon steam cracking containing the following steps: (a) preparing an aqueous solution by mixing Cr containing compound and Zr containing compound or Cr—Zr containing compound with water; (b) impregnating a carrier in the prepared aqueous solution; and (c) preparing a composite catalyst containing the oxide component by sintering the impregnated carrier.

At this time, in the step (a), a metal compound containing one or more selected from the group consisting of Ti, Nb, Mo, V, Co, Ni, W, Fe and rare earth metals, or the Cr containing compound or the Zr containing compound or the Cr—Zr containing compound can additionally include one or more selected from the group consisting of Ti, Nb, Mo, V, Co, Ni, W, Fe and rare earth metals, and preferably the compound contains Ti additionally.

The carrier is selected from the group consisting of alpha alumina, silica, silica-alumina, zirconium oxide, magnesium oxide, magnesium aluminate, calcium aluminate, silicon carbide, aluminum titanate and zeolite, and silicon carbide is preferred.

The present invention provides a method of preparing olefin containing the step of hydrocarbon steam cracking in the presence of a catalyst selected from the group consisting of a composite catalyst prepared by sintering the mixture of powder of the oxide catalyst represented by $CrZr_jA_kO_x$ ($0.5 \leq j \leq 120$, $0 \leq k \leq 50$, A is a transition metal, x is the number satisfying the condition according to valences of Cr, Zr and A, and values of j and k) and carrier powder, and a catalyst having the oxide catalyst impregnated on a carrier.

At this time, A of the oxide is one or more selected from the group consisting of Ti, Nb, Mo, V, Co, Ni, W, Fe and rare earth metals, and Ti is preferred.

The carrier is selected from the group consisting of alpha alumina, silica, silica-alumina, zirconium oxide, magnesium oxide, magnesium aluminate, calcium aluminate, silicon carbide, aluminum titanate and zeolite, and silicon carbide is preferred.

Hereinafter, the present invention is described in detail.

The present inventors completed this invention by confirming that when an oxide containing Cr and Zr or an oxide containing Cr and Zr and one or more metals selected from the group consisting of Ti, Nb, Mo, V, Co, Ni, W, Fe and rare earth metals was used as a catalyst component and molded with a carrier, the catalytic activity was increased compared with the conventional art, olefin yield was increased, inactivation rate by coke was reduced, possibility of deformation at high temperature was lowered owing to the excellent thermal/mechanical stability and the problems of the conventional art such as decrease of hydrocarbon decomposing activity and unsatisfactory light olefin yield could be overcome.

As for the catalyst for hydrocarbon steam cracking of the present invention, two different types of catalysts can be used. One of the two is the composite catalyst prepared by sintering the mixture of the oxide catalyst powder represented by $CrZr_jA_kO_x$ and carrier powder, and the other of the two is the composite catalyst having the oxide catalyst represented by $CrZr_jA_kO_x$ impregnated on a carrier.

The catalytic component of the catalyst for hydrocarbon steam cracking is characteristically represented by formula 1.

$$CrZr_jA_kO_x \quad \text{[Formula 1]}$$

Wherein, $0.5 \leq j \leq 120$, preferably $5 \leq j \leq 90$, more preferably $70 \leq j \leq 90$, $0 \leq k \leq 50$, preferably, $5 \leq k \leq 30$, more preferably $15 \leq k \leq 28$, A is a transition metal, x is the number satisfying the condition according to valences of Cr, Zr and A, and values of j and k.

And, A contains one or more metals selected from the group consisting of Ti, Nb, Mo, V, Co, Ni, W, Fe and rare earth metals.

The catalyst for hydrocarbon steam cracking of the present invention can contain a catalyst component represented by formula 2 which corresponds to when k of formula 1 is 0.

$$CrZr_jO_x \quad \text{[Formula 2]}$$

Wherein, $0.5 \leq j \leq 120$, preferably $5 \leq j \leq 90$, more preferably $70 \leq j \leq 90$, and x is the number satisfying the condition according to valences of Cr and Zr and j value.

When it is used for hydrocarbon steam cracking, the catalyst of the present invention not only increases the reaction yield but also improves the selectivity of light olefin, specifically propylene, and maintains thermo-stability.

When hydrocarbon steam cracking is performed at 800° C., the preferable ratio of the ethylene/propylene is 1.5-1.7. When the reaction temperature is increased more than 800° C., propylene selectivity begins to decrease.

The method of preparing the catalyst for hydrocarbon steam cracking of the present invention characteristically contains the following steps: (a) preparing an aqueous solution by mixing Cr containing compound and Zr containing compound or Cr—Zr containing compound with water; (b) preparing a slurry by co-precipitation after adding ammonia water to the prepared aqueous solution; (c) heat-refluxing or hydrothermal-treating the slurry; (d) preparing an oxide catalyst by filtering the slurry, drying and calcining thereof; (e) preparing a composite catalyst by sintering the mixture of the oxide catalyst powder and carrier powder; (f) molding the composite catalyst; and (g) sintering the molded composite catalyst.

In step (a), an aqueous solution is prepared by mixing a metal compound with water.

The Cr containing compound and Zr containing compound or Cr—Zr containing compound can be a salt such as sulfate, nitrate, oxalate, halide or chloride, and nitrate is more preferred.

The metal compound such as Cr containing compound and Zr containing compound or Cr—Zr containing compound can be further mixed with the third metal compound. And herein, the third metal compound is a metal compound which can be one or more compounds selected from the group consisting of Ti, Nb, Mo, V, Co, Ni, W, Fe and rare earth metals, and particularly Ti, Ni and rare earth metals are preferred and Ti and Y are more preferred.

The Cr containing compound, the Zr containing compound or the Cr—Zr containing compound are the third metal compound, which can include one or more selected from the group consisting of Ti, Nb, Mo, V, Co, Ni, W, Fe and rare earth metals, and particularly Ti, Ni and rare earth metals are preferred and Ti and Y are more preferred.

Each metal component of the third metal compound can be salt, acid, oxide, hydroxide or alkoxide, etc. If a metal component of the third metal compound is an alkoxide precursor, the alkoxide is hydrolyzed in water and educed as a solid salt. Therefore, a strong acid such as nitric acid is necessarily added to dissolve the salt.

After dissolving the metal component of the third metal compound in water, this solution can be mixed with Cr and Zr aqueous solutions. Or the metal component can be dissolved in water together with Cr and Zr precursors.

The aqueous solution containing the components is heated and stirred at 40-80° C., preferably 60-70° C. for at least one hour until all the components are mixed completely.

In step (b), ammonia is added to the aqueous solution of step (a). PH of the solution is preferably regulated to 7-9, more preferably 8-8.5, followed by coprecipitation to prepare slurry.

In step (c), the slurry prepared in step (b) is heat-refluxed at the same temperature as mentioned in step (a) for at least 12 hours or hydrothermal-treated via autoclave at 60-150° C.

In step (d), the slurry heat-refluxed or hydrothermal-treated in step (c) is filtered, dried and calcined to give a catalyst.

The drying is preferably performed at 120° C. for at least 2 hours.

The calcination herein is preferably performed at 750-1600° C. for at least 4 hours. If the calcining temperature is maintained in the range, sintering is not hurry, so that catalytic activity is less reduced.

In step (e), the oxide catalyst powder represented by formula 1 or formula 2 prepared in step (d) is mixed with carrier powder, followed by sintering. The preferable content of the oxide catalyst component in the total weight of the composite catalyst is 0.5-50 weight %, which is the preferable content facilitating hydrocarbon steam cracking. If the content is less than 0.5 weight %, the oxide catalyst component cannot be fully functioning as a catalyst. In the meantime, if the content is more than 50 weight %, the strength of the catalyst is reduced. A binder can be additionally added during the mixing of the oxide catalyst component and a carrier.

The carrier herein can be any conventional carrier selected from the group consisting of alpha alumina, silica, silica-alumina, zirconium oxide, magnesium oxide, magnesium aluminate, calcium aluminate, silicon carbide, aluminum titanate and zeolite, and silicon carbide is preferred. When silicon carbide is used as a carrier, the precursors of silicon carbide, silicon and carbon, can be mixed with the oxide catalyst component. At this time, silicon and carbon, the precursors, are changed into silicon carbide during the sintering process of step (g).

In step (f), the composite catalyst of step (e) is molded in a specific form. For the molding, compression molding or extrusion molding is performed.

In step (g), the molded product in a specific shape, prepared in step (f), is sintered. The molded product of step (f) becomes smaller in volume during the sintering, resulting in a composite catalyst having a right size, density and surface area. The sintering is performed at the temperature of at least 1200° C. for at least 2 hours.

The composite catalyst finished with the sintering above preferably has the density of 0.5~3.5 g/cm$^3$, the surface area of up to 50 m$^2$/g and the compressive strength of at least 1000N.

Another method of preparing the catalyst for hydrocarbon steam cracking of the present invention comprises the following steps: (a) preparing an aqueous solution by mixing Cr containing compound and Zr containing compound or Cr—Zr containing compound with water; (b) impregnating a carrier in the prepared aqueous solution; and (c) preparing a composite catalyst containing the oxide component by sintering the impregnated carrier. As a result, the catalyst harboring the oxide catalyst component represented by formula 1 or formula 2, which is a composite catalyst, is prepared.

In step (a), an aqueous solution is prepared by mixing a metal compound with water.

The Cr containing compound and Zr containing compound or Cr—Zr containing compound can be a salt such as sulfate, nitrate, oxalate, halide or chloride, and nitrate is more preferred.

The metal compound such as Cr containing compound and Zr containing compound or Cr—Zr containing compound can be further mixed with the third metal compound. And herein, the third metal compound is a metal compound which can be one or more compounds selected from the group consisting of Ti, Nb, Mo, V, Co, Ni, W, Fe and rare earth metals, and particularly Ti, Ni and rare earth metals are preferred and Ti and Y are more preferred.

The Cr containing compound, Zr containing compound or Cr—Zr containing compound is the third metal compound, which can includes one or more selected from the group consisting of Ti, Nb, Mo, V, Co, Ni, W, Fe and rare earth metals, and particularly Ti, Ni and rare earth metals are preferred and Ti and Y are more preferred.

Each metal component of the third metal compound can be salt, acid, oxide, hydroxide or alkoxide, etc. If a metal component of the third metal compound is an alkoxide precursor, the alkoxide is hydrolyzed in water and educed as a solid salt. Therefore, a strong acid such as nitric acid is necessarily added to dissolve the salt.

After dissolving the metal component of the third metal compound in water, this solution can be mixed with Cr and Zr aqueous solutions. Or the metal component can be dissolved in water together with Cr and Zr precursors.

The aqueous solution containing the components is heated and stirred at 40-80° C., preferably 60-70° C. for at least one hour until all the components are mixed completely.

In step (b), the aqueous solution is impregnated on a carrier by incipient wetness impregnation or liquid impregnation, followed by drying (at 120° C. for at least 10 hours) to prepare a carrier loaded with a catalyst precursor.

Calcination is preferably performed at 800-1400° C. for at least 6 hours.

The composite catalyst finished with calcining preferably contains the oxide catalyst component of 0.5-30 weight % by the total weight of the composite catalyst for the successful hydrocarbon steam cracking. If the content is less than 0.5 weight %, the catalytic activity is in doubt. If the content is more than 30 weight %, the catalytic effect is inefficient.

At this time, the carrier can be any conventional carrier selected from the group consisting of alpha alumina, silica, silica-alumina, zirconium oxide, magnesium oxide, magnesium aluminate, calcium aluminate, silicon carbide, aluminum titanate and zeolite. Among these carriers, silicon carbide having compressive strength of at least 1000 N is more preferred.

The method of preparing light olefin of the present invention is characterized by using the catalyst for hydrocarbon steam cracking prepared by the above method for hydrocarbon steam cracking.

The light olefin of the present invention indicates olefin having up to 4 carbons, particularly exemplified by ethylene and propylene.

The hydrocarbon steam cracking for the production of light olefin is preferably performed at 600-1000° C., weight ratio of water vapor/hydrocarbon of 0.3-1.0 and space velocity (LHSV) of 1-20 $hr^{-1}$.

In this reaction, a fixed bed reactor, a fluidized bed reactor or a mobile phase reactor can be used. In particular, when a fixed bed reactor is used, a round shaped or pellet catalyst can be used, but at this time, differential pressure in the catalyst layer becomes bigger, which is a problem. To overcome this problem, a catalyst is preferably molded in the shape of Raschig or in any other specific shapes to increase porosity in the catalyst layer.

BRIEF DESCRIPTION OF THE DRAWINGS

The application of the preferred embodiments of the present invention is best understood with reference to the accompanying drawings, wherein.

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

A mixed aqueous solution was prepared by dissolving 2.96 g of chrome nitrate hydrate and 8.93 g of zirconia nitrate hydrate in water. Ammonia water was dropped slowly to the prepared mixed aqueous solution, during which pH was regulated as 8, followed by coprecipitation and then heat-refluxing for 12 hours. The coprecipitated aqueous solution was filtered and washed with water. The catalyst was separated therefrom. Moisture was eliminated by drying the catalyst in a drier. The dried catalyst was calcined at 800° C. for 6 hours in air atmosphere.

The catalyst produced above was confirmed to have the composition of $CrZr_5O_x$.

Example 2

An experiment was performed by the same manner as described in Example 1 except that the calcination was performed at 1200° C.

Example 3

2.68 g of titanium isopropoxide was dissolved in water and nitric acid was slowly dropped in the solution with stirring until it came clear. 12.35 g of zirconia nitrate hydrate and 0.24 g of chrome nitrate hydrate were added thereto, resulting in the mixed aqueous solution. Ammonia water was dropped slowly to the mixed aqueous solution, during which pH was regulated as 8, followed by coprecipitation and then heat-refluxing for 12 hours. The coprecipitated aqueous solution was filtered and washed with water. The catalyst was separated therefrom. Moisture was eliminated by drying the catalyst in a drier. The dried catalyst was calcined at 800° C. for 6 hours in air atmosphere.

The catalyst produced above was confirmed to have the composition of $CrZr_{83.3}Ti_{16.7}O_x$.

Example 4

An experiment was performed by the same manner as described in Example 3 except that the calcination was performed at 1200° C.

Example 5

The catalyst prepared in Example 3 was used for the hexane contacting steam cracking for 5 hours under the same conditions as described in the following Experimental Example and then the catalyst was recovered and regenerated by burning coke for 6 hours in air atmosphere.

Example 6

The catalyst powder prepared in Example 3 was mixed with the silicon carbide powder of Comparative Example 3, followed by vacuum sintering. The catalyst finished with the sintering according to the procedure contained $CrZr_{83.3}Ti_{16.7}O_x$ by 5, 10 and 15 weight % for the weight of silicon carbide.

Example 7

The catalyst powder prepared in Example 3 was mixed with silicon and carbon powder, followed by vacuum sintering. The catalyst finished with the sintering according to the procedure contained $CrZr_{83.3}Ti_{16.7}O_x$ by 5, 10 and 15 weight % for the weight of silicon carbide.

Example 8

2.68 g of titanium isopropoxide was dissolved in water and nitric acid was slowly dropped in the solution with stirring until it came clear. 12.35 g of zirconia nitrate hydrate and 0.24 g of chrome nitrate hydrate were added thereto, resulting in the mixed aqueous solution. The mixed aqueous solution was impregnated in a silicon carbide carrier by incipient wetness impregnation. The catalyst prepared by impregnating a catalyst precursor solution in silicon carbide was dried in a drier, followed by calcining at 800° C. for 6 hours. The catalyst finished with the calcination according to the above procedure contained $CrZr_{83.3}Ti_{16.7}O_x$ by 10 weight % for the weight of silicon carbide.

Comparative Example 1

500 μm sized α-alumina having 99.5% purity was used herein.

Comparative Example 2

An aqueous solution was prepared by dissolving 15.87 g of magnesium nitrate hydrate, 4 g of potassium hydroxide and 7.12 g of ammonium phosphate in water. The mixed aqueous solution was dried by vacuum distillation using a vacuum evaporator to obtain a catalyst. The catalyst was dried in a drier, followed by calcining at 1100° C. for 6 hours.

The catalyst produced above was confirmed to have the composition of $KMgPO_4$.

Comparative Example 3

500 μm sized silicon carbide having 99.5% purity was used herein.

Experimental Example 1

The catalysts prepared in Examples 1-8 and Comparative Example 1-3 were used for hydrocarbon steam cracking according to the following methods.

Hexane was used as hydrocarbon. A quartz tube of ¼" in external diameter was filled with the catalyst up to 5 cm in height and the reaction temperature was maintained as 750° C. The injection ratio of hexane to water was 2:1 and the flow speed of hexane was adjusted to LHSV of 5 $hr^{-1}$. Hexane and water were injected by using a syringe pump. Hexane and water were evaporated respectively at 400° C. and at 500° C. using a vaporizer to be ready for the contact with the catalyst layer. At this time, contact between the gas and the catalyst layer was made when the two gases were well mixed. The product discharged from the rector was quantified by gas chromatography and the yield of the product was calculated according to the following Mathematical Formula 1.

Yield of the product (weight %)=weight of the product/weight of the injected hexane×100    [Mathematical Formula 1]

Example 9

The catalyst powder prepared in Example 3 was mixed with silicon carbide powder, followed by vacuum sintering. The catalyst finished with the sintering according to the procedure contained $CrZr_{83.3}Ti_{16.7}O_x$ by 10 weight % for the weight of silicon carbide and had density of 1.34 $g/cm^3$.

Comparative Example 4

Silicon carbide having 99.5% purity and density of 2.6 $g/cm^3$ was used herein.

Experimental Example 2

Ethylene and propylene were produced using the catalysts prepared in Example 9 and Comparative Example 4 by the following method. Naphtha was used as hydrocarbon for hydrocarbon steam cracking and the composition and physical property of the naphtha used herein are shown in Table 1.

TABLE 1

| Physical Property | | | | | | |
|---|---|---|---|---|---|---|
| | | | Composition (weight %) | | | |
| Density (g/cc) | Initial boiling point (° C.) | Terminal boiling point (° C.) | n-paraffin | l-paraffin | Naphthene | Aromatic compound |
| 0.675 | 30.9 | 160.7 | 39.5 | 38.9 | 15.3 | 6.3 |

Naphtha and water were added to the reactor by using a metering pump. At this time, the addition weight ratio of naphtha to water was 2:1. The flow rate of naphtha was adjusted to 10 $hr^{-1}$ of LHSV. Naphtha and water added to the reactor were mixed after passing through the evaporator and then passed through the first preheater heated at 550° C., followed by passing through the second preheater heated at 650° C. The mixture was then injected in the reactor (length: 300 cm, diameter: 4.3 cm) filled with the catalyst.

The reactor was heated by electric furnace. The water vapor-naphtha mixture passed through the second preheater was cracked while it passed through the reactor. The outlet temperature of the reactor (reaction temperature) was regulated between 740~820° C. but maintained at 800° C. upon completion of the reaction. The reaction products passed through two condensers connected serially, during which water and heavy oil were condensed and separated as a liquid phase and the remaining gas phase mixture was analyzed by gas chromatography connected online, followed by elimination. The naphtha cracking procedure continued for 120 hours and coke was burned at 800° C. in water vapor-air atmosphere to regenerate the catalyst. The naphtha cracking-coke burning process repeated two more times, completing the three-cycle reaction in total. The yield of ethylene was calculated by the following Mathematical Formula 2 and the yield of another product (propylene) was calculated by the same method.

Yield of ethylene (weight %)=amount of produced ethylene/amount of injected naphtha×100    [Mathematical Formula 2]

TABLE 2

| | | Composition | calcining temperature (° C.) | Yield (weight %) | | | Conversion rate (weight %) |
|---|---|---|---|---|---|---|---|
| | | | | Ethylene | Propylene | Ethylene + propylene | |
| Example | 1 | $CrZr_5O_x$ | 800 | 23.04 | 19.30 | 42.34 | 73.93 |
| | 2 | $CrZr_5O_x$ | 1200 | 22.48 | 15.84 | 38.32 | 61.21 |
| | 3 | $CrZr_{83.3}Ti_{16.7}O_x$ | 800 | 24.39 | 20.18 | 44.57 | 75.12 |
| | 4 | $CrZr_{83.3}Ti_{16.7}O_x$ | 1200 | 24.10 | 18.07 | 42.17 | 67.69 |
| | 5 | $CrZr_{83.3}Ti_{16.7}O_x$ | 800 | 23.92 | 19.60 | 43.52 | 72.70 |
| Comparative Example | 1 | α-alumina | — | 22.27 | 14.30 | 36.57 | 60.42 |
| | 2 | $KMgPO_4$ | 1100 | 23.36 | 14.80 | 38.16 | 59.94 |

As shown in Table 2, the catalyst of the present invention which is the oxide catalyst containing Cr and Zr (Example 1) exhibited approximately 14 weight % increased conversion rate of hexane decomposition, compared with Comparative Example 1 using α-alumina, and approximately 6 weight % increased olefin yield owing to its Cr—Zr oxide complex structure providing catalytic active site that favors the catalytic activity in hydrocarbon steam cracking. The oxide catalyst containing Cr and Zr of the present invention is more effective in hydrocarbon cracking to produce light olefin, in particular to produce propylene, than the conventional catalyst $KMgPO_4$ of Comparative Example 2.

The catalyst prepared in Example 3 by calcining the oxide catalyst containing Cr and Zr and a transition metal such as Ti exhibited a little increased catalytic activity and as a result increased light olefin selectivity and yield thereof. Compared with the catalyst of Example 1, the conversion rate of hexane decomposition was approximately 1.2 weight % increased and olefin yield was also approximately 2.2 weight % increased.

Hydrocarbon steam cracking was performed at about 800° C. but the catalyst could be exposed on much higher temperature temporarily or locally by hot-spot generated during the burning process to eliminate coke generated on the inside wall of the reactor or the surface of the catalyst. Therefore, a catalyst having an excellent thermostability is required so as to maintain its catalytic activity at high temperature of at least 1000° C.

The catalyst of Example 2 prepared by calcining the oxide catalyst containing Cr and Zr, the catalytic components of the present invention, at 1200° C. exhibited reduced hexane decomposing activity and as a result light olefin yield was reduced approximately 4 weight %, compared with the catalyst of Example 1. However, compared with α-alumina of Comparative Example 1, this catalyst exhibited still high catalytic activity.

The catalyst of Example 4 prepared by mixing with Cr and Zr and additionally Ti and calcining at 1200° C. exhibited a little reduced catalytic activity compared with the catalyst of Example 3, but the selectivity of light olefin was excellent. Thus, the yield of olefin was 5.6 weight % higher than that of the reaction using α-alumina of Comparative Example 1. The catalyst of Example 5, regenerated by burning coke generated on the surface of the catalyst after hydrocarbon steam cracking at high temperature maintained its catalytic activity. The oxide catalyst containing Cr and Zr and Ti was confirmed to be very stable at high temperature of at least 1200° C. and at the same time at low temperature of up to 1000° C. and has excellent catalytic activity.

TABLE 3

| | | Yield (weight %) | | | Conversion rate (weight %) |
|---|---|---|---|---|---|
| | Composition | Ethylene | Propylene | Ethylene + propylene | |
| Example 6 | 5% $CrZr_{83.3}Ti_{16.7}O_x$ + SiC | 23.01 | 14.91 | 37.91 | 60.22 |
| | 10% $CrZr_{83.3}Ti_{16.7}O_x$ + SiC | 23.89 | 15.62 | 39.52 | 62.17 |
| | 15% $CrZr_{83.3}Ti_{16.7}O_x$ + SiC | 24.89 | 15.95 | 40.83 | 64.1 |
| Example 7 | 5% $CrZr_{83.3}Ti_{16.7}O_x$ + Si + C | 22.26 | 13.6 | 35.86 | 56.26 |
| | 10% $CrZr_{83.3}Ti_{16.7}O_x$ + Si + C | 22.34 | 14.06 | 36.4 | 57.51 |
| | 15% $CrZr_{83.3}Ti_{16.7}O_x$ + Si + C | 22.82 | 14.48 | 37.3 | 59.59 |
| Example 8 | 10% $CrZr_{83.3}Ti_{16.7}O_x$ + SiC | 22.87 | 14.95 | 37.82 | 60.32 |
| Comparative Example 3 | SiC | 21.34 | 13.73 | 35.06 | 55.86 |

As shown in Table 3, the composite catalyst containing the oxide catalyst component having the composition of $CrZr_{83.3}Ti_{16.7}O_x$ and the carrier silicon carbide of Example 6 exhibited improved light olefin (ethylene, propylene) yield, compared with the silicon carbide of Comparative Example 3 not having the active site. As the content of $CrZr_{83.3}Ti_{16.7}O_x$ increased, light olefin yield increased. When the content of $CrZr_{83.3}Ti_{16.7}O_x$ was increased up to 15 weight %, light olefin yield was increased 5.8 weight %. The catalyst of Example 7 prepared by mixing the oxide having the composition of $CrZr_{83.3}Ti_{16.7}O_x$ and silicon and carbon exhibited a little increased light olefin yield compared with the catalyst of Comparative Example 3 but showed lower conversion rate and light olefin yield than the catalyst of Example 6. Therefore, it is suggested that silicon carbide carrier is preferred to prepare a composite catalyst with the oxide having the composition of $CrZr_{83.3}Ti_{16.7}O_x$ and silicon carbide.

The yield of light olefin was increased not only by using the catalyst prepared from the mixture of the oxide having the composition of $CrZr_{83.3}Ti_{16.7}O_x$ and silicon carbide and sintering thereof but also by using the catalyst prepared by impregnating the catalyst component in a molded silicon carbide carrier. The catalyst of Example 8, in which 10 weight % of $CrZr_{83.3}Ti_{16.7}O_x$ was impregnated in the silicon carbide carrier, exhibited higher olefin yield than the catalyst of Example 7 (compared with equal amount of each catalyst) but lower olefin yield than the catalyst of Example 6. The composite catalysts of examples demonstrated high catalytic activity and selectivity even after calcining at high temperature of at least 1200° C. In particular, the composite catalyst of Example 6 exhibited excellent light olefin selectivity without any catalytic activity loss.

TABLE 4

|  | Cycle No. | Reaction Temperature (° C.) | Yield (weight %) | | | Ethylene/propylene ratio |
|---|---|---|---|---|---|---|
|  |  |  | Ethylene | Propylene | Ethylene + propylene |  |
| Example 9 | 1 | 740 | 16.8 | 15.09 | 31.89 | 1.11 |
|  | 1 | 780 | 25.26 | 17.25 | 42.51 | 1.46 |
|  | 1 | 800 | 27.06 | 16.78 | 43.84 | 1.61 |
|  | 1 | 820 | 31.89 | 14.83 | 46.72 | 2.15 |
|  | 2 | 800 | 26.16 | 16.32 | 42.48 | 1.60 |
| Comparative Example 4 | 1 | 740 | 15.94 | 14.34 | 30.28 | 1.11 |
|  | 1 | 780 | 22.97 | 14.05 | 37.02 | 1.63 |
|  | 1 | 800 | 26.32 | 13.56 | 39.88 | 1.94 |
|  | 1 | 820 | 29.79 | 12.41 | 42.2 | 2.4 |

As shown in Table 4, the composite catalyst of Example 9 prepared by mixing the oxide catalyst component having the composition of $CrZr_{83.3}Ti_{16.7}O_x$ and the carrier silicon carbide could increase light olefin (ethylene, propylene) yield up to 1.5-4.5 weight %, compared with silicon carbide not having the active site used in Comparative Example 4. As reaction temperature was raised, light olefin yield increased and the catalyst was more effective in producing propylene than in producing ethylene. However, when reaction temperature was at least 800° C., propylene yield began to decrease. Therefore, to drive propylene at the best mode, temperature was preferably set at 780~800° C.

In the cracking process, the ratios of methane/propylene and ethylene/propylene are indexes indicating not only the toughness of the cracking process but also the light olefin selectivity.

As shown in Table 4, when the cracking was performed at 800° C., the ratio of ethylene/propylene of Example 9 was 1:61 and that of Comparative Example 4 was 1.94. That is, the ratio of ethylene/propylene became lower when the composite catalyst of Example 9 was used, compared with when silicon carbide was used in Comparative Example 4, suggesting that the catalyst of Example 9 was more effective in increasing propylene selectivity.

Figure 1:
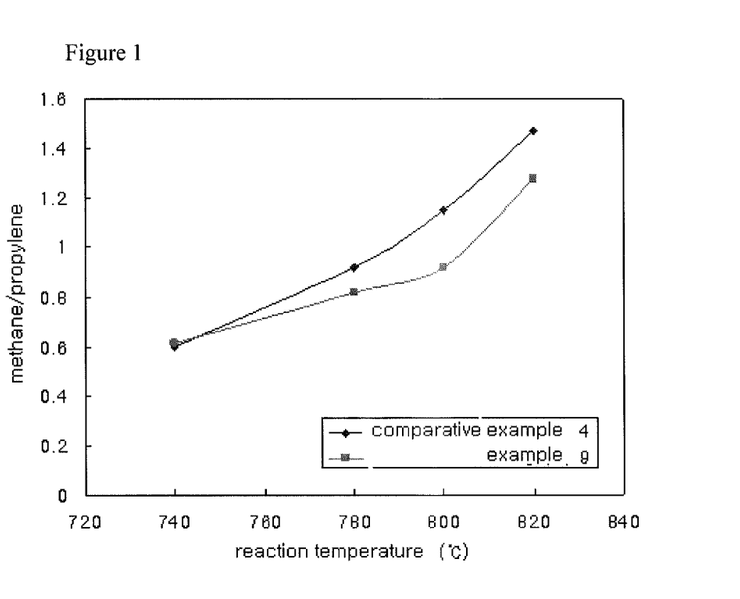
FIG. 1 illustrates the ratios of the reaction products methane/propylene produced from hydrocarbon steam cracking reaction of the present invention by using different catalysts which are the composite catalyst of Example 9 and silicon carbide of Comparative Example 4.
Figure 2:
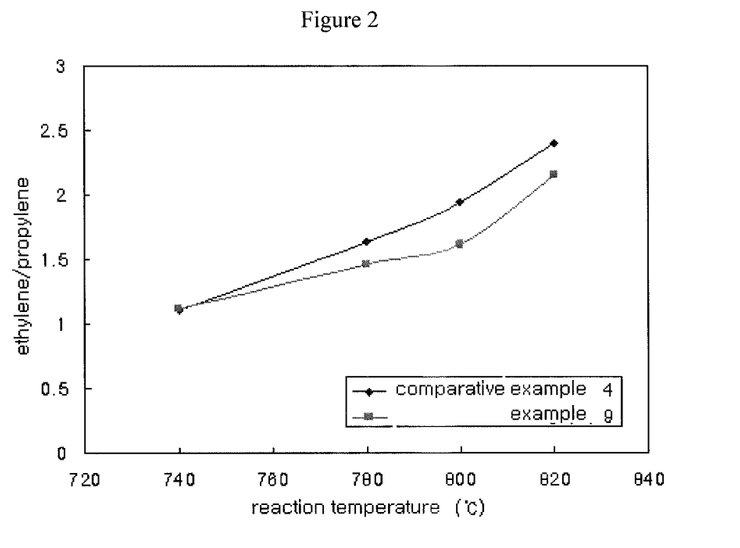
FIG. 2 illustrates the ratios of the reaction products ethylene/propylene produced from hydrocarbon steam cracking reaction of the present invention by using different catalysts which are the composite catalyst of Example 9 and silicon carbide of Comparative Example 4.

As shown in FIG. 1 and FIG. 2, the composite catalyst of Example 9 exhibited lower methane/propylene ratio and ethylene/propylene ratio than silicon carbide of Comparative Example 4 showed. That is, high propylene ratio in the equal amount of produced methane suggests that propylene selectivity increases. Low ethylene/propylene ratio indicates that this catalyst favors propylene production. The silicon carbide of Comparative Example 4 has no such active site and only induced cracking. In the meantime, the composite catalyst of Example 9 has the effect of increasing ethylene and propylene yields, particularly favors the improvement of propylene selectivity.

Figure 3:
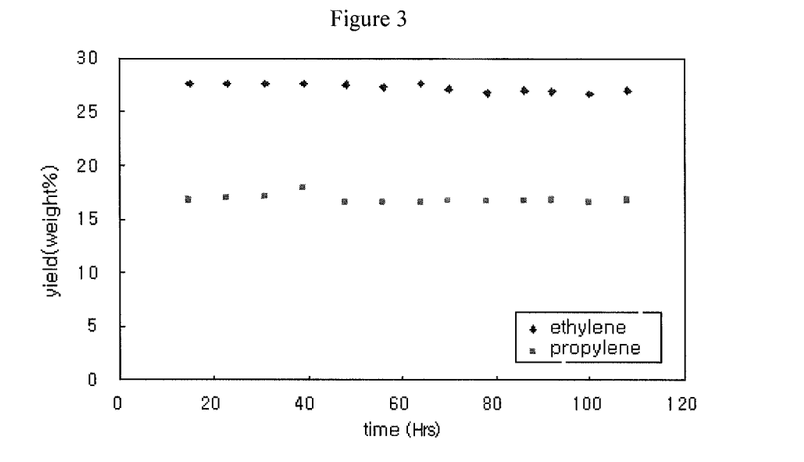
FIG. 3 illustrates the yields of ethylene and propylene, the products from hydrocarbon steam cracking reaction of the present invention, over the driving time when the composite catalyst of Example 9 is used.

In the high temperature naphtha decomposition, coke deposition on the surface of a catalyst and inside of the reactor is unavoidable. So, the decrease of olefin yield by coke deposition during the cracking process is necessarily expected but when the composite catalyst of Example 9 prepared by the method of the present invention is used for the reaction, catalytic activity is almost maintained without loss for the whole operating time of 120 hours, as shown in FIG. 3. This is because coke deposition on silicon carbide used as a carrier is hardly observed and the coke deposition on the wall of the reactor is also significantly reduced.

Hydrocarbon steam cracking is performed at around 800° C. But, to eliminate coke generated on the surface of the catalyst or inside wall of the reactor, burning is necessary, during which the catalyst can be exposed temporarily or locally on very high temperature by hot spot. So, a catalyst having excellent thermostability is highly recommended to maintain catalytic activity during hydrocarbon steam cracking being performed at the temperature of at least 1000° C. The composite catalyst of Example 9 prepared by the method of the present invention recovered one-cycle of catalytic activity even after being regenerated by burning coke generated on the surface of the catalyst at high temperature after naphtha decomposition. After completing 3 cycles, the composite catalyst showed no thermal/physical changes and maintained the primary mechanical strength.

The composite catalyst of Example 9 was confirmed to be stable at up to 1000° C. and at the same time at high temperature of at least 1200° C. and has low inactivation rate but excellent catalytic activity.

INDUSTRIAL APPLICABILITY

As explained hereinbefore, the catalyst for hydrocarbon steam cracking of the present invention has excellent thermal/mechanical stability at high temperature, has low inactivation rate by coke, and has the effect of improving light olefin selectivity and yield.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A hydrocarbon steam cracking catalyst comprising a composite catalyst including an oxide catalyst represented by $CrZr_jA_kO_x$, wherein $5 \leq j \leq 120$, $5 \leq k \leq 30$, A is one or more transition metal selected from the group consisting of Ti, Mo, V, and Co and x is the number satisfying the condition according to valences of Cr, Zr and A, and values of j and k, and a carrier, wherein the carrier is selected from the group consisting of magnesium aluminate, calcium aluminate, silicon carbide, aluminum titanate and zeolite, and wherein the content of the oxide catalyst is 0.5-30 weight % by the total weight of the composite catalyst.

2. The catalyst for hydrocarbon steam cracking according to claim 1, wherein the composite catalyst has the density of 0.5~3.5 g/cm3, the surface area up to 50 m2/g and the compressive strength of at least 1000 N.

3. The catalyst for hydrocarbon steam cracking according to claim 1, wherein the A of the oxide is Ti.

4. The catalyst for hydrocarbon steam cracking according to claim 1, wherein the carrier is silicon carbide.

5. The catalyst according to claim 1, wherein steam cracking is performed in the presence of the catalyst for hydrocarbon steam cracking at 800° C. and the weight ratio of products ethylene/propylene is 1.5-1.7.

6. The hydrocarbon steam cracking catalyst of claim 1, wherein the composite catalyst is prepared by impregnating the oxide catalyst on a carrier.

7. The catalyst according to claim 6, wherein the oxide catalyst is prepared using a mixture of a Cr containing compound selected from the group containing sulfate, nitrate, oxalate, halide and chloride of chromium, a Zr containing selected from the group containing sulfate, nitrate, oxalate, halide and chloride of Zr, and an alkoxide of A.

8. The hydrocarbon steam cracking catalyst of claim 1, wherein the composite catalyst is prepared by sintering the oxide catalyst and the carrier.

9. The catalyst according to claim 8, wherein the oxide catalyst is prepared using a mixture of a Cr containing compound selected from the group containing sulfate, nitrate, oxalate, halide and chloride of chromium, a Zr containing selected from the group containing sulfate, nitrate, oxalate, halide and chloride of Zr, and an alkoxide of A.

10. A hydrocarbon steam cracking catalyst comprising a composite catalyst prepared by mixing an oxide catalyst powder represented by $CrZr_jA_kO_x$, wherein $5 \leq j \leq 120$, $5 \leq k \leq 30$, A is one or more transition metal selected from the group consisting of Mo, V, and Co and x is the number satisfying the condition according to valences of Cr, Zr and A, and values of j and k, and a carrier powder and sintering the same,
wherein the content of the oxide catalyst powder is 0.5-30 weight % by the total weight of the composite catalyst.

11. A hydrocarbon steam cracking catalyst comprising a composite catalyst prepared by impregnating an oxide catalyst represented by $CrZr_jA_kO_x$, wherein $5 \leq j \leq 120$, $5 \leq k \leq 30$, A is one or more transition metal selected from the group consisting of Mo, V, and Co and x is the number satisfying the condition according to valences of Cr, Zr and A, and values of j and k, on a carrier,
wherein the content of the oxide catalyst is 0.5-30 weight % by the total weight of the composite catalyst.

* * * * *